(12) United States Patent
O'Lenick, Jr.

(10) Patent No.: US 6,521,220 B2
(45) Date of Patent: Feb. 18, 2003

(54) POLYMERIC CASTOR POLYESTER QUATERNARY COMPOUNDS

(75) Inventor: Anthony J. O'Lenick, Jr., Dacula, GA (US)

(73) Assignee: Zenitech LLC, Old Greenwich, CT (US)

( * ) Notice: Subject to any disclaimer, the term of this patent is extended or adjusted under 35 U.S.C. 154(b) by 86 days.

(21) Appl. No.: 09/849,703

(22) Filed: May 7, 2001

(65) Prior Publication Data

US 2003/0007950 A1 Jan. 9, 2003

(51) Int. Cl.[7] .................. A61K 7/075; C08G 63/02; C08G 63/40
(52) U.S. Cl. .................. 424/70.28; 424/64; 424/401; 528/272; 528/275; 528/288; 528/295.5
(58) Field of Search .................. 424/401, 64, 70.28; 528/272, 275, 288, 295.5

(56) References Cited

U.S. PATENT DOCUMENTS 5,786,389 A * 7/1998 O'Lenick et al.
6,342,527 B1 * 1/2002 O'Lenick et al. ........... 424/401

* cited by examiner

Primary Examiner—Jyothsan Venkat

(57) ABSTRACT

The present invention deals with the certain castor polyesters that give high gloss when applied to the skin. Said ester are the reaction of the hydroxyl group of castor oil with less than one equivalent of a fatty acid then in a subsequently step the remainder of an equivalent of a diacid.

12 Claims, No Drawings

POLYMERIC CASTOR POLYESTER QUATERNARY COMPOUNDS

BACKGROUND OF THE INVENTION

1. Field of the Invention

The present invention deals with the use of certain novel polyester quaternary compounds that are prepared by the sequential reaction of castor oil with isostearic acid to provide an intermediate that is esterified with a diacid to provide a polyester, then in a subsequent step reacted with a castor quat. In addition, the present invention describes a process for providing gloss to the skin, which comprises application of an effective glossing concentration of this polyester and softness and gloss to hair.

2. Description of the Art Practices

There is a desire to develop an ester that gives gloss to the skin when applied from oils or applied from emulsions and gloss and conditioning to the hair when so applied. An added aspect of the present invention is the fact that the compounds are polymeric. This has two very important implications on the use of the materials of the present invention. The polymeric nature means the compounds do not penetrate the skin. The fact that these molecules remain on the hair or skin, increases gloss and provides a less irritation to the hair or skin. They also provide a gloss that is more long lasting.

U.S. Pat. No. 5,786,389 issued July 1998 to O'Lenick, incorporated herein by reference, describes the use of a guerbet ester of castor for gloss, The compounds are a simple ester made by the reaction of castor and a specific mono functional alcohol to produce an ester. The products of this patent are neither polymeric, nor do they involve reaction of the hydroxyl group in the castor molecule. We have discovered that higher gloss, lower irritation and better durability of gloss results when one makes the polymers of the present invention.

Until the compounds of the present invention polyesters did not give a sufficient gloss when applied to the hair and skin. None of the prior esters possess the critical combination of branching and the polymeric composition unique to castor. The quaternary nature (i.e. the + charge) makes the compounds more substantive to hair and provides unexpected durability of the conditioning.

THE INVENTION

This invention relates to a series of polyester quaternary compounds derived from castor oil. Castor oil, a hydroxy containing oil, can be esterified with a fatty acid to produce an intermediate having both an ester and triglyceride functionality. By selecting the ratios of reactants, the castor can be a partially substituted with fatty acid leaving some unreacted hydroxyl groups. The number of remaining hydroxyl groups, and the type and concentration of diacid used to react with the unreacted hydroxyl groups, results in a controllable polyester. The control of molecular weight and degree of polymerization is critical to functionality of the product.

The unique structure of castor oil coupled with the proper selection of the fatty acid and diacid chosen to make the polyester results in a product that has unique gloss when applied to skin. One of the unique aspects of the present invention is the fact that the reaction to make an ester is conducted on the castor hydroxyl group, not the triglyceride group. Another unique aspect of the present reaction is the selection of a proper mole ratio to leave unreacted hydroxyl groups present in each triglyceride to crosslink the product, providing a polyester.

Specifically, the present invention discloses novel polyesters and a process for providing gloss to the skin that comprises application of an effective glossing concentration of an polyester conforming to the following structure:

$$A-(B)x-A$$

wherein

A is:

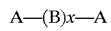

B is;

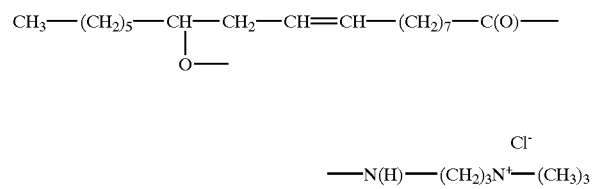

wherein;

R' is —C(O)—CH$_2$CH$_2$—C(O)—;

a is an integer ranging from 2 to 10.

R is selected from alkyl and alkylene having 5 to 33 carbon atoms;

x is an integer ranging from 1 to 50.

In a simple case where x is 1 the following polymer results:

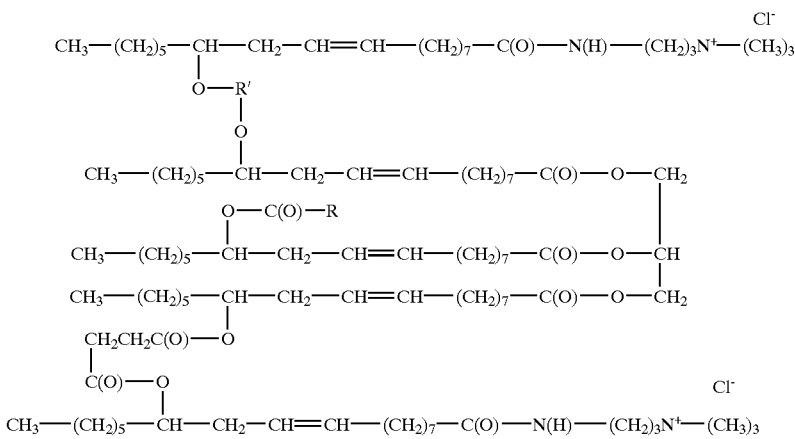

By varying the ratio of fatty acid more of the hydroxyl group is left. In the case of the "A" unit, two of the three hydroxyl groups on the castor oil are reacted, leaving only one group left to react. In the case of the "B" units two hydroxyl groups are left to react. In making a one pot synthesis, the total number of acid groups is calculated any reacted in the first step with the castor oil, followed by the reaction of the remaining hydroxyl groups with diacid. In some instances it is desirable to leave some unreacted hydroxyl groups in the polymer. The quat group, being monofunctional with regard to hydroxyl group is the chain terminator. That is it is the "A" group in the molecule.

PREFERRED EMBODIMENTS

In a preferred embodiment x is an integer ranging from 3 to 5.

In a preferred embodiment x is an integer ranging from 5 to 10.

In a preferred embodiment R is alkylene having 11 to 21 carbon atoms.

In a preferred embodiment R is alkyl having 7 to 10 carbon atoms.

In a preferred embodiment R is alkylene having 17 carbon atoms.

EXAMPLES

Raw Materials

Castor Oil

Castor oil is a unique triglyceride. It is derived from Ricinus Communis L. The castor plant grows wild in many subtropical and tropical areas. Today Brazil, China and India provide over 90% of the oil. Castor oil contains a large content of hydroxy containing compounds that are unsaturated. The common name for the predominant species in castor is ricinoleic acid. More correctly it is called 12-hydroxy-9 octadecenoic acid or d-12-hydroxyoleic acid.

The acid conforms to the following structure:

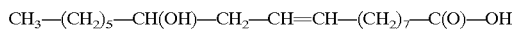

Castor Oil is a clear, viscous, light colored fluid that is nondrying and quite stable. The Purity of Castor Oil occurs with remarkable uniformity. Regardless of country of origin, or season it is grown, the composition and chemical properties remain within a very narrow range. Castor Oil has a CAS Number of 8001-79-4 and an EINECS Number of 232-293-8.

Castor oil has a unique carbon distribution, which has 18 carbon atoms and one double bond. The concentration of that species is about 90% by weight. It is this ricinoleic moiety that when linked to a guerbet alcohol in an ester gives unique gloss when applied to the skin.

Linoleic acid has the unusual property of having both a double bond that results in a specific conformation of the "kinked carbon chain" placing the hydroxyl group in a locked position. While not professing only one mechanism of action, it is believed that the introduction of the polar guerbet branched portion of the molecule results in an ester that has a great deal of branching. The molecule takes on a conformation having the minimum free energy. That conformation places the polar hydroxyl groups from different molecules into an associative complex. This complex is delivered to the skin either neat or in emulsions giving a great deal of gloss that is durable. There are many cosmetic applications in which gloss is desirable.

Fatty Acids

Fatty Acids are items of commerce, available in pure form and in mixtures. One of manufacturer offering a very wide range of products of high quality is Cognis, formerly Henkel Corporation.

Fatty acids have common names. They also have a commonly used shorthand used to describe them. The designation is a letter "C" and a number indicating the number of carbon atoms in the molecule. If no additional information is offered the product is saturated. If a ":" follows and a number after it the product has the specified number of double bonds in the molecule. Consequently, C6 is a saturated six carbon fatty acid. C12:1 is a 12 carbon fatty acid having one double bond.

| Example | Designation and Name | | Formula |
|---|---|---|---|
| 1 | C6 | Caproic acid | $C_6H_{12}O_2$ |
| 2 | C8 | Caprylic acid | $C_8H_{16}O_2$ |

-continued

| Example | Designation | and Name | Formula |
|---|---|---|---|
| 3 | C10 | Capric acid | $C_{10}H_{20}O_2$ |
| 4 | C12 | Lauric acid | $C_{12}H_{24}O_2$ |
| 5 | C12:1 | Lauroleic acid | $C_{12}H_{22}O_2$ |
| 6 | C14 | Myristic acid | $C_{14}H_{28}O_2$ |
| 7 | C14:1 | Myristoleic acid | $C_{14}H_{26}O_2$ |
| 8 | C16 | Palmitic acid | $C_{16}H_{32}O_2$ |
| 9 | C16:1 | Palmitoleic acid | $C_{16}H_{30}O_2$ |

| Example | Designation | and Name | Formula |
|---|---|---|---|
| 10 | C18 | Stearic acid | $C_{18}H_{36}O_2$ |
| 11 | C18:1 | Oleic acid | $C_{18}H_{34}O_2$ |
| 12 | C18:2 | Linoleic acid | $C_{18}H_{32}O_2$ |
| 13 | C18:3 | Linolenic acid | $C_{18}H_{30}O_2$ |
| 14 | C20 | Arachidic acid | $C_{20}H_{40}O_2$ |
| 15 | C20:1 | Gadoleic acid | $C_{20}H_{38}O_2$ |
| 16 | C22 | Behenic acid | $C_{22}H_{44}O_2$ |
| 17 | C22:1 | Erucic acid | $C_{22}H_{42}O_2$ |
| 18 | C22:2 | Clupanodinic acid | $C_{22}H_{40}O_2$ |
| 19 | C24 | Lignoceric acid | $C_{24}H_{48}O_2$ |
| 20 | C26 | Cerotic acid | $C_{26}H_{52}O_2$ |
| 21 | C28 | Montanic acid | $C_{28}H_{56}O_2$ |
| 22 | C30 | Myricic acid | $C_{30}H_{60}O_2$ |
| 23 | C32 | Lacceroic acid | $C_{32}H_{64}O_2$ |
| 24 | C34 | Geddic acid | $C_{34}H_{68}O_2$ |

Succinic Acid

Succinic acid is an item of commerce and conforms the following structure:

Castor Quat

The castor quat useful in the preparation of the compounds of the present invention are commercially available from Siltech Corporation, Toronto Ontario Canada and several others. It conforms to the following structure:

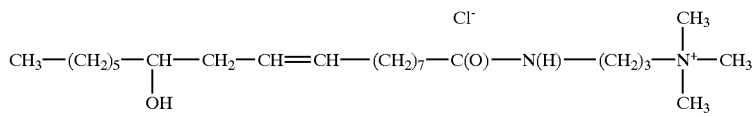

Ester Synthesis

The esterification reaction is carried out using the proper amounts of fatty acid, castor oil and castor quat. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure

To 846.0 grams of castor oil is added the specified amount of the specified fatty acid (examples 1–24). Next add 0.1% stannous oxylate based upon the total weight of the batch after all ingredients have been charged, under agitation. The temperature of the mass is raised to 195–200 C. off. The reaction mass is held at this temperature for between 4 and 15 hours, until the acid value drops to vanishingly small values.

Next the specified amount of succinic acid is added. The reaction mass is kept between 195 and 200 C. for an additional 4 to 15 hours until the acid value ceases to fall further. The resulting product is a clear oil that is used without additional purification.

Examples 25–48

| | | Fatty Acid | | Succinic Acid |
|---|---|---|---|---|
| Example | "x" Value | Example | Grams | Grams |
| 25 | 1 | 1 | 64.4 | 50.0 |
| 26 | 1 | 2 | 80.0 | 50.0 |
| 27 | 3 | 3 | 80.3 | 150.0 |
| 28 | 5 | 4 | 85.7 | 250.0 |
| 29 | 4 | 5 | 88.0 | 200.0 |
| 30 | 10 | 6 | 88.7 | 500.0 |
| 31 | 50 | 7 | 78.2 | 2500.0 |
| 32 | 1 | 8 | 142.2 | 50.0 |
| 33 | 3 | 9 | 118.5 | 150.0 |
| 34 | 3 | 10 | 132.5 | 150.0 |
| 35 | 4 | 11 | 125.3 | 200.0 |
| 36 | 5 | 12 | 120.0 | 250.0 |
| 37 | 6 | 13 | 115.8 | 300.0 |
| 38 | 3 | 14 | 145.6 | 150.0 |
| 39 | 4 | 15 | 137.8 | 200.0 |
| 40 | 5 | 16 | 145.7 | 250.0 |
| 41 | 2 | 17 | 169.0 | 100.0 |
| 42 | 1 | 18 | 186.7 | 50.0 |
| 43 | 4 | 19 | 46.2 | 200.0 |
| 44 | 5 | 20 | 169.7 | 250.0 |
| 45 | 6 | 21 | 176.7 | 300.0 |
| 46 | 7 | 22 | 184.1 | 350.0 |
| 47 | 1 | 23 | 266.7 | 50.0 |
| 48 | 5 | 24 | 217.7 | 250.0 |

Capping with Castor Quat

Next add 494.0 grams of castor quat is added. The reaction mass is kept between 195 and 200 C. for an additional 4 to 15 hours until the acid value ceases to fall further. The resulting product is a clear oil that is used without additional purification.

Examples 49–67

| Example | Intermediate Example |
|---|---|
| 49 | 25 |
| 50 | 26 |
| 51 | 27 |
| 52 | 28 |
| 53 | 29 |
| 54 | 30 |
| 55 | 31 |
| 56 | 32 |
| 57 | 33 |
| 58 | 34 |
| 59 | 35 |
| 60 | 36 |
| 61 | 37 |

-continued

| Example | Intermediate Example |
|---------|---------------------|
| 62 | 38 |
| 63 | 39 |
| 64 | 40 |
| 62 | 41 |
| 66 | 42 |
| 67 | 43 |

Applications Examples

The effective glossing concentration of the products of the present invention range from 0.05% to 30% by weight. The preferred concentration ranges from 1 to 10%. The compounds of the present invention are formulated into lipsticks and color cosmetics where they provide a high gloss to the skin and into conditioning creams for hair applications.

The compounds can be emulsified and applied from aqueous systems using emulsification techniques known to those skilled in the art.

The compounds of the present invention can be applied to the hair to provide outstanding gloss.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A polyester conforming to the following structure:

A—(B)$x$—A wherein

A is:

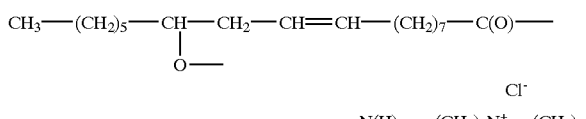

B is;

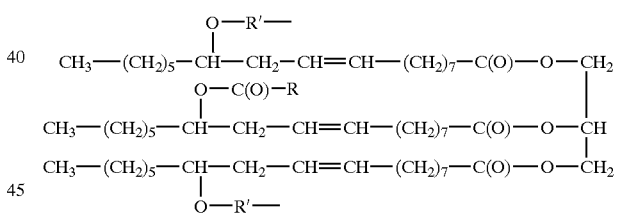

wherein;

R' is —C(O)—CH$_2$CH$_2$—C(O)—;

a is an integer ranging from 2 to 10;

R is selected from alkyl and alkylene having 5 to 33 carbon x is an integer ranging from 1 to 50.

2. A compound of claim 1 wherein x is an integer ranging 3 to 5.

3. A compound of claim 1 wherein x is an integer ranging 5 to 10.

4. A compound of claim 1 wherein R is alkylene having 11 to 21 carbon atoms.

5. A compound of claim 1 wherein R is alkyl having 7 to 10 carbon atoms.

6. A compound of claim 1 wherein R is alkylene having 17 carbon atoms.

7. A process for providing gloss to hair and skin which comprises contacting the hair or skin with an effective glossing concentration of a polyester conforming to the following structure:

A—(B)$x$—A wherein

A is:

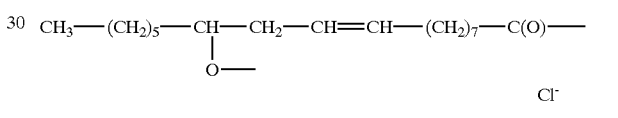

B is;

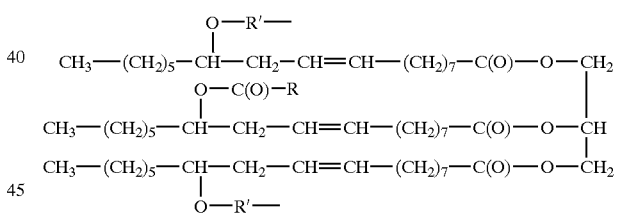

wherein;

R' is —C(O)—CH$_2$CH$_2$—C(O)—;

a is an integer ranging from 2 to 10;

R is selected from alkyl and alkylene having 5 to 33 carbon atoms;

x is an integer ranging from 1 to 50.

8. A process of claim 7 wherein x is an integer ranging from 3 to 5.

9. A process of claim 7 wherein x is an integer ranging from to 5 to 10.

10. A process of claim 7 wherein R is alkylene having 11 to 21 carbon atoms.

11. A process of claim 7 wherein R is alkyl having 7 to 10 carbon atoms.

12. A process of claim 7 wherein R is alkylene having 17 carbon atoms.

* * * * *